(12) United States Patent
Salem et al.

(10) Patent No.: US 9,557,299 B2
(45) Date of Patent: Jan. 31, 2017

(54) ADAPTIVE DATA COLLECTION FOR LOCAL STATES OF A MATERIAL

(71) Applicant: MRL Materials Resources LLC, Dayton, OH (US)

(72) Inventors: Ayman A. Salem, Beavercreek, OH (US); Daniel P. Satko, Centerville, OH (US); Joshua B. Shaffer, Centerville, OH (US)

(73) Assignee: MRL MATERIALS RESOURCES LLC, Dayton, OH (US)

( * ) Notice: Subject to any disclaimer, the term of this patent is extended or adjusted under 35 U.S.C. 154(b) by 498 days.

(21) Appl. No.: 14/209,719

(22) Filed: Mar. 13, 2014

(65) Prior Publication Data
US 2014/0260623 A1 Sep. 18, 2014

Related U.S. Application Data

(60) Provisional application No. 61/780,789, filed on Mar. 13, 2013.

(51) Int. Cl.
| | | |
|---|---|---|
| *G01N 21/00* | (2006.01) | |
| *G01N 29/04* | (2006.01) | |
| *G01N 23/20* | (2006.01) | |
| *G01N 23/22* | (2006.01) | |
| *G01N 29/44* | (2006.01) | |

(52) U.S. Cl.
CPC .............. *G01N 29/04* (2013.01); *G01N 23/20* (2013.01); *G01N 23/22* (2013.01); *G01N 29/4472* (2013.01)

(58) Field of Classification Search
CPC ........ G01N 33/00; G01N 23/20; G01N 23/22; G01N 29/04; G01N 21/64; G01N 21/68; G01N 2015/1037; H01J 37/32935; G01J 3/02
See application file for complete search history.

(56) References Cited

U.S. PATENT DOCUMENTS

| | | | |
|---|---|---|---|
| 7,716,987 B2 | 5/2010 | Sathish et al. | |
| 2006/0111644 A1* | 5/2006 | Guttag | A61B 5/048 |
| | | | 600/544 |

OTHER PUBLICATIONS

R. Smith et al., "Orientation Imaging Using Spatially Resolved Acoustic Spectroscopy", Journal of Physics: Conference Series 353 (2012), 10th Anglo-French Physical Acoustics Conference (AFPAC 2011), IOP Publishing, DOI: 10.1088/1742-6596/353/1/012003.

* cited by examiner

*Primary Examiner* — Abdullahi Nur
(74) *Attorney, Agent, or Firm* — Thomas E. Lees, LLC

(57) ABSTRACT

According to aspects of the present disclosure, features of interest in materials are analyzed. The method comprises capturing a morphology of the feature of interest on a surface or an interior of a material under evaluation. The method also comprises selecting targeted spatial locations on the surface or the interior of the material under evaluation based upon the captured morphology. Also, the method comprises capturing information about the local state (e.g., crystallographic orientation) of the surface or the interior of the sample at the selected targeted spatial locations. Still further, the method comprises using the captured local state information to fill in the non-targeted spatial locations in the material corresponding to the captured morphology and or topology.

20 Claims, 10 Drawing Sheets

ADAPTIVE DATA COLLECTION FOR LOCAL STATES OF A MATERIAL

CROSS-REFERENCE TO RELATED APPLICATIONS

This application claims the benefit of U.S. Provisional Patent Application Ser. No. 61/780,789, filed Mar. 13, 2013, entitled ADAPTIVE DATA COLLECTION FOR LOCAL STATES OF A MATERIAL, the disclosure of which is hereby incorporated by reference.

BACKGROUND

The present disclosure relates to the analysis of materials, and in particular to techniques for the efficient data collection of the local states of a material.

Materials science deals with the fundamental properties and characteristics of materials. For instance, the field of materials science often attempts to explore the relationship between the structure of materials at atomic or molecular scales (i.e., microstructure), as well as the macroscopic properties of such materials. By studying how different processes affect materials, and by studying how such materials perform under different conditions, an understanding of the limitations and capabilities of materials can be identified and predicted.

BRIEF SUMMARY

According to aspects of the present disclosure, a method is provided for capturing detailed information about the local state within various microstructural features of interests in materials, e.g., on the surfaces or within the interior of the material. The method comprises capturing a morphology of features of interest of a material under evaluation. For instance, the morphology may capture shapes of various constituents on a surface and/or capture information within the bulk of the material under evaluation. Also, the method comprises obtaining information giving the local state of the material under evaluation at various spatial locations that correspond to the captured morphology. For instance, the method may capture detailed information on the local state (e.g., crystallographic orientation) of the surface of the sample at the selected regions within the same area of the material in which the morphology was (or is to be) captured. In this regard, the order in which the morphology is captured, and the local state information is obtained, may not be important. Still further, the method comprises using the obtained local state information to fill spatial locations of the material under evaluation where local state information was not obtained, at locations that correspond to the captured morphology.

In certain illustrative implementations, the local state of the material under evaluation may be obtained by selecting targeted spatial locations of the material under evaluation based upon the captured morphology. For instance, the method may select targeted regions (i.e., features of interest) on the surface (or inside the bulk) of the material under evaluation based upon the captured morphology to obtain the local state of the material. The method may also comprise performing a rendering operation using the captured local state information to fill in the non-targeted spatial locations comprising each feature of interest of the material under evaluation.

Figure 1:
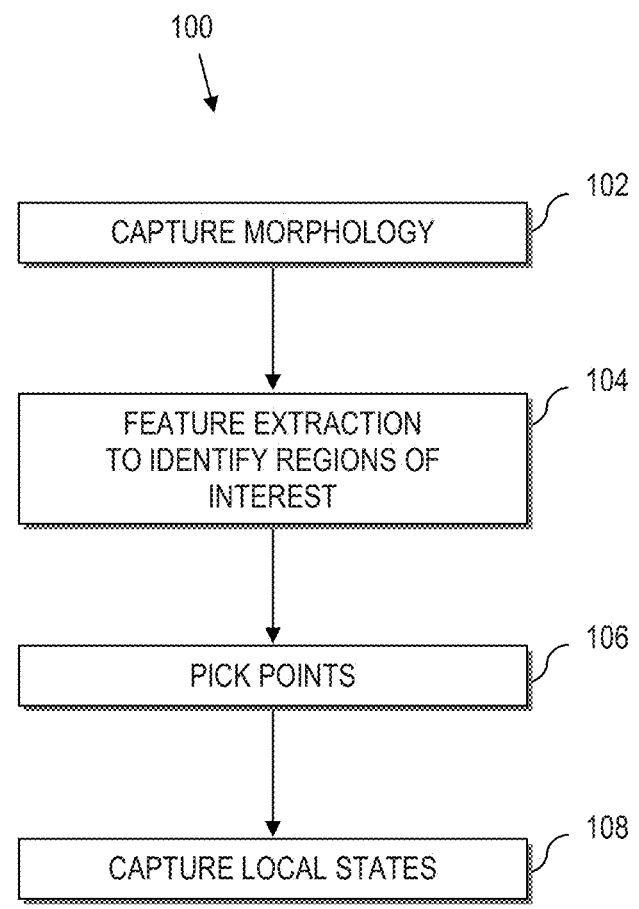
FIG. 1 is a flow chart illustrating a process for the adaptive data collection of the local states of a material under evaluation, according to aspects of the present disclosure.

In the following detailed description, reference is made to the accompanying drawings, which form a part hereof, and in which is shown by way of illustration, and not by way of limitation, specific embodiments in which the disclosure may be practiced. It is to be understood that other embodiments may be utilized and that changes may be made without departing from the spirit and scope of the present disclosure.

DETAILED DESCRIPTION

Due to the strong effect of microstructure on the mechanical behavior of a material, it may be important to have a clear understanding of the various constituents of the microstructure (including crystallographic orientation) and their influence on the mechanical behavior and other properties, as well as the evolution of such constituents and properties under a broad range of loading conditions.

In general, a material's local state (e.g., crystallographic orientation, chemistry, etc.) is captured. By way of example, α-β titanium alloys exhibit rich details that span several hierarchical length scales. In this regard, in certain implementations, the local state may be thought of as an element of the local state space that identifies the complete set of distinct local states that could theoretically be encountered at the selected length scale. The local state can be defined as a combination of several microstructure variables. For example, at the scale of individual grains, the local state may include the thermodynamic phase, the elemental composition of the phase, and the crystal lattice orientation. As such, the local state and the corresponding local state space may be inherently tied to the length and time scales salient to the physics of the phenomena under consideration.

For instance, a determination of the local states of a material involves the application of a stimulus (e.g., visible light, electron beam, X-rays, ultrasound waves, mechanical loading) and measurement of the subsequent response (e.g., reflectance, scattering, diffraction, displacement) to give information about the desired local state of interest (e.g., crystallographic orientation, chemistry, mechanical properties). However, producing measurements of the local states of a material over a large area (e.g., >1 mm$^2$) and with sufficient resolution to identify features at multiple length scales, is hampered either by the high cost of the measurements (e.g., using electron beam or x-ray stimulus) or insufficient spatial resolution of the technique (e.g., ultrasound stimulus).

Certain microstructures have constituents with distinct morphologies that can be extracted using standard image segmentation techniques. For instance, extracting details of the microstructure of α-β titanium alloys such as alpha laths in the lamellar microstructure or alpha particles in an equiaxed microstructure can be implemented using a contrast threshold in imaging software to distinguish between the appearance of the alpha laths/particles and the surrounding beta matrix. However, a bimodal microstructure creates a challenge because the alpha phase has two morphological constituents, primary alpha particles and secondary alpha colonies with alternating alpha laths and beta layers. Because both constituents have an identical crystal structure, measurements of crystallographic orientation cannot automatically distinguish between the two morphological constituents. Rather, the use of multimodal signals and thresholding techniques are typically required to segment primary alpha particles and secondary alpha colonies based on measurements of solute partitioning, typically using x-ray techniques inside a scanning electron microscope. However, applying these methods to large areas for practical applications is expensive and time consuming.

According to various aspects of the present disclosure, the local state information of a material is captured such that the collection and analysis (e.g., the quantification, identification or both) of features of interest (FOI) (e.g., particles, grains, colonies, macrozones, microtextured regions, etc.) in the material can be carried out in an expedited manner, according to one or more approaches set out herein. Moreover, approaches are provided for efficient data collection of the local states of a material under evaluation, which can utilize high speed, high resolution equipment.

For instance, the material's local state may be captured by collecting a plurality of individual measurements of the local state. For instance, the measurements may be taken with reference to spatial locations on the sample surface or within the sample interior, e.g., at various spatial locations that correspond to the captured morphology. The measurements are collected using any suitable measurement device. For example, a measurement device may comprise a combination of stimulus (e.g., electron beam, x-ray, ultrasound, etc.) and a response measurement device (e.g., electron backscatter diffraction detector, secondary electron (SE) detector, energy dispersive spectroscopy detector, CCD camera, film, transducer, etc.). In alternative implementations, the material's local state is captured via recorded data, modeled data, projected data, etc.

The measurements taken with the response measurement device constitute a number of measurements less than the total number of measurement that are needed to cover the whole area within a feature of interest (e.g., grain, particle, etc.) in the material under evaluation. However, by collecting specifically targeted response measurements (i.e., local states) at designed spatial locations within certain features of interest, the methods herein can intelligently "fill in" the local state information into otherwise unmeasured spatial locations in a manner that presents an extremely high likelihood that the actual local state of the material at that spatial location matches the "filled-in" (i.e., rendered) local state information. In this way, the "feature of interest (FoI)" is defined as a contiguous bounded region within which the local state may be assumed to be constant or having a variation less than some defined threshold.

One illustrative example of a FoI is the concept of a "grain" in metallic or ceramic materials. In general, a grain refers to a spatial region having a similar or nearly similar crystallographic crystal orientation (i.e., local state) bounded and separated from other grains, having a different crystallographic orientation, by a grain boundary. Such grain boundaries can be observed by various techniques (e.g., optical microscopy of etched samples), giving information about the morphology of the FoI (e.g., grains).

The identification of a FoI results from the analysis of topological and/or morphological measurements of the material of interest (surface, interior, or both).

As used throughout the specification and claims, the term "morphology" in all of its forms (e.g., morphology, morphological, etc.) is intended to include morphology, topology, e.g., with details about the shapes, boundaries of specific microstructural features of interest, or any combination thereof, unless otherwise specifically stated.

The morphological measurements can be carried out using the same stimulus as the stimulus used to carry out the local state measurements. Alternatively, the morphological measurements can be carried out using a different stimulus. Similarly, the morphological measurements can be captured using the same detector used to capture the local state measurements. Alternatively, the morphological measurements can be captured using a different response detector. For example, grain morphology in titanium alloys can be captured using a secondary electron (SE) detector or backscattered electron (BSE) detector whereas local crystallographic orientations can be captured using electron backscatter diffraction (EBSD) detector, where both grain morphology and local crystallographic orientations can be captured using the same stimulus, i.e., an electron beam inside a scanning electron microscope. In another example, grain morphology in titanium alloys can be captured using a CCD or CMOS camera attached to a light optical microscope whereas local crystallographic orientations can be captured using electron backscatter diffraction (EBSD) detector, where grain morphology and local crystallographic orientations are captured using different stimuli, e.g., a visible light beam and an electron beam, respectively. As such, the morphology and the local state information can be collected in any order, either independently or dependently.

Morphological measurements tend to be conducted at high resolution at faster speeds while local state measurements (e.g., orientations) tend to be conducted at low resolution and/or low speed. However, such is not required by the approaches set out herein.

The measurements, including "filled-in" local state measurements, are logically organized into a plurality of "tiles" such that each tile includes a number of measurements. Each measurement (in whatever form is provided by the particular response measurement technology) is mapped to a structure that allows subsequent processing, referred to herein generally for sake of discussion as a "local state vector". Thus, there is a local state vector for each pixel of each tile.

Overall Flow Diagram:

Referring now to the drawings, and particularly to FIG. 1, a flow diagram illustrates a process 100 for measuring and analyzing (e.g., identifying, quantifying, etc.) the morphology of features of interest in material surfaces (or interior bulk) according to aspects of the present disclosure.

A morphology is captured at 102. As noted in greater detail herein, the morphology can be captured in two dimensions (e.g., on a polished surface, unpolished surface, an etched surface, an interior surface of the material, etc.), or in three dimensions, (e.g., so as to be an interior volume, a surface or both). As further examples, the morphology may be captured as a mechanical model, electrical model, thermodynamic model, crystallographic model, thermal model, acoustic model, etc.

The method 100 also comprises obtaining information giving the local state of the material under evaluation at various spatial locations that correspond to the captured morphology. For instance, one exemplary manner of obtaining information giving the local state of the material under evaluation is by performing at 104, feature extraction on the morphological data to identify features of interest. Notably, feature extraction to identify a feature of interest need not be directly carried out in the captured data. Rather, the features of interest can be identified based upon a recognized feature in the captured data, or using data analytics, or in any other manner in which a feature, e.g., pattern or other aspect can be discerned.

Moreover, the local states do not necessarily directly identify the microstructure features of interest. As such, automated protocols for the extraction of selected features of interest may be utilized to obtain consistency and reproducibility independent of operator bias and with minimum computational cost. Moreover, computer vision algorithms built on supervised and unsupervised machine learning techniques may be employed for automated feature identification and extraction.

Regardless, to extract specific FoI, some or all components of a local state vector can be used in a cluster analysis. For example, for identifying only the beta phase in alpha-beta titanium alloys, a single variable in the local state vector (e.g., bcc (body-centered cubic) phase in EBSD dataset) is adequate. However, segmenting primary alpha grains in bimodal microstructures may require clustering data regarding crystallographic orientation, chemistry, and/or imaging contrast at each pixel in the microstructure dataset.

According to illustrative implementations, a feature of interest may be defined as a region in physical space that depicts similar characteristic local state vectors as some other regions in the microstructure. This definition enables setting up automated extraction tools that are mainly dependent on the components of the local state vector. For instance, to achieve automation and to increase the speed of extraction, the identification may be conducted in a two-step process in two separate domains. The first step is conducted in the local state vector domain (i.e., local state space), in which volumes with similar local state vectors are classified using cluster analysis. The second step is conducted in physical space by mapping the classified clusters from the first step to corresponding spatial locations in real space.

Within a FoI, one or more points are selected at 106 and the local state is captured at 108 for each selected point. For instance, information giving the local state of the material under evaluation may be captured by crystallography, chemistry, an acoustic model, an elastic model, an electrical model, etc.

The method 100 may also comprise using the obtained local state information to fill spatial locations of the material under evaluation where local state information was not obtained, at locations that correspond to FoI in the captured morphology.

Figure 2:
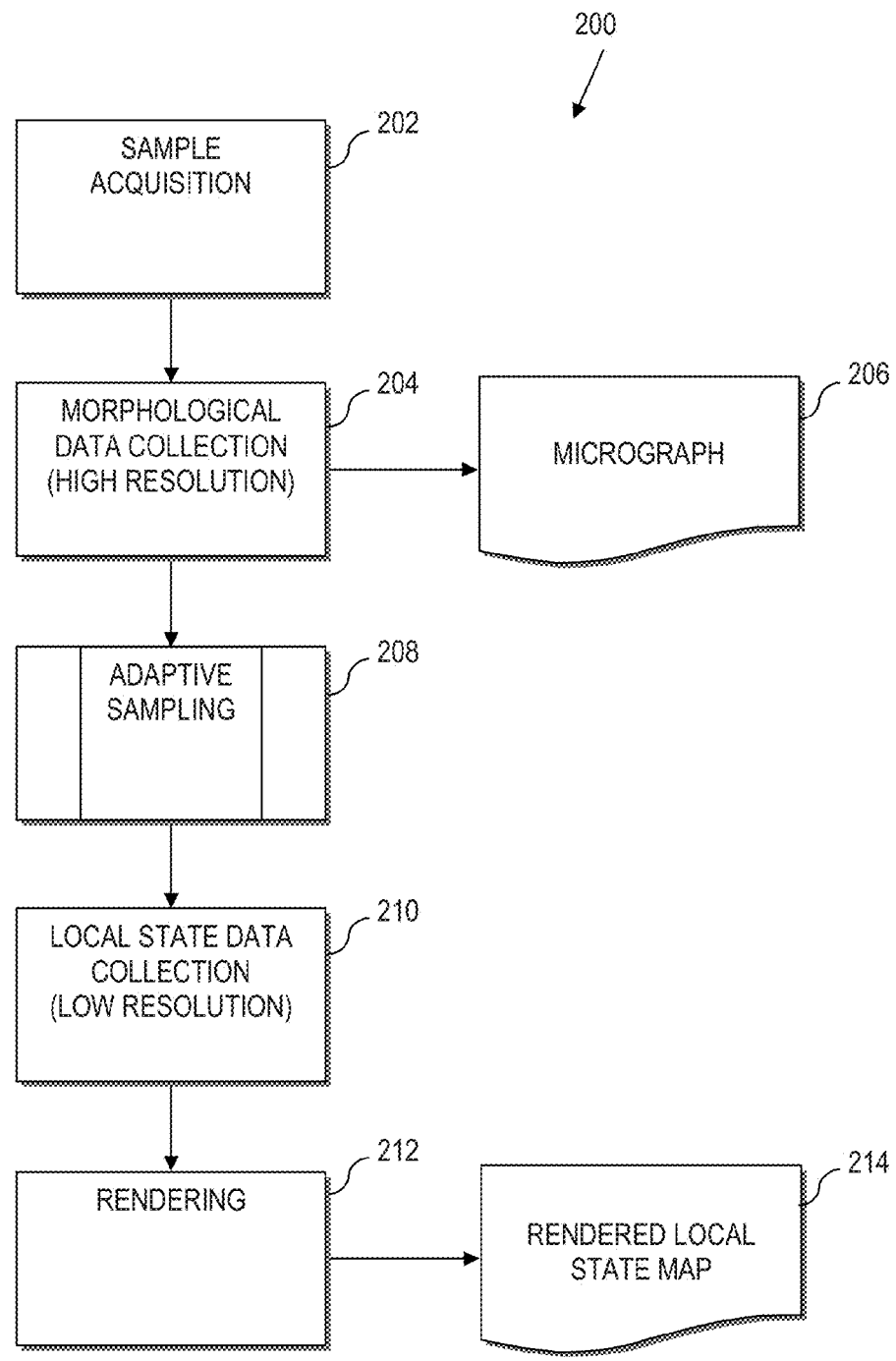
FIG. 2 is a flow chart illustrating a process for the adaptive data collection of the local states of a material under evaluation, according to further aspects of the present disclosure.

Referring to FIG. 2, a flow diagram illustrates a process 200 for measuring and analyzing (e.g., identifying, quantifying, etc.,) the morphology of features of interest in material surfaces (or interior bulk), according to further aspects of the present disclosure. Thus, the process 200 illustrates an example of implementing the method 100 described with reference to FIG. 1.

For example, a sample acquisition process at 202 captures morphologies of features of interest at 204 on a surface of a material under evaluation. By way of illustration, the morphology may be captured using optical microscopy. As another example, using light as a stimulus, grain morphologies can be captured via optical micrographs at 206. In this regard, the optical microscopy provides a reasonably fast and efficient way to obtain high-resolution images of a sample with various features of interest enclosed by grain boundaries. In exemplary applications, the sample comprises a polished and etched surface to reveal the grain boundaries, e.g., for the analysis and evaluation of metals such as titanium. However, in practice, the sample may comprise a polished surface, unpolished surface, an etched surface, an interior surface of the material, etc. In another example, a process is utilized to capture morphologies of different phases in a material (e.g., titanium alloys) using a scanning electron microscope equipped with a backscattered electron (BSE) detector that reveals the morphology of various FoI (e.g., phases) based on the atomic number of each phase.

Figure 3:
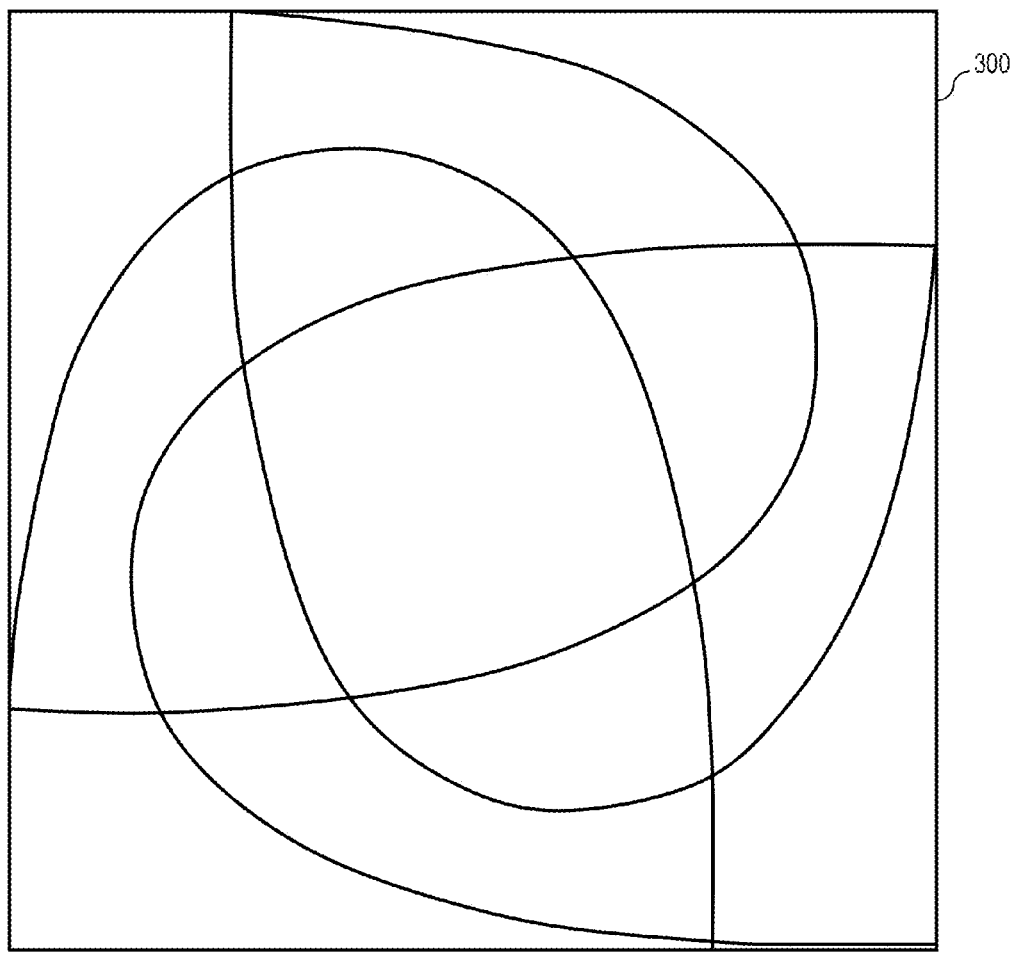
FIG. 3 is an exemplary illustration of captured microstructure morphology from a surface of a sample, where a feature of interest is shown to be contained within an area that is marked by the sketched black boundaries, according to aspects of the present disclosure.

Referring briefly to FIG. 3, an illustration demonstrates an example captured microstructure morphology 300 from a surface of a sample. According to aspects of the present disclosure, several features of interest are shown to be contained within an area that is marked by the sketched black boundaries.

Referring back to FIG. 2, the process performs adaptive sampling at 208, generating a data collection scheme to obtain information giving the local state of the material under evaluation at various spatial locations that correspond to the captured morphology. In an illustrative example, at 208, based upon the captured morphology, the adaptive sampling selects targeted regions within each feature of interest on the surface of the material (or in the interior of the bulk) under evaluation. The process further captures local material states at 210, such as crystallographic orientation information of the surface of the sample at the selected spatial locations in the targeted features of interest.

Figure 4:
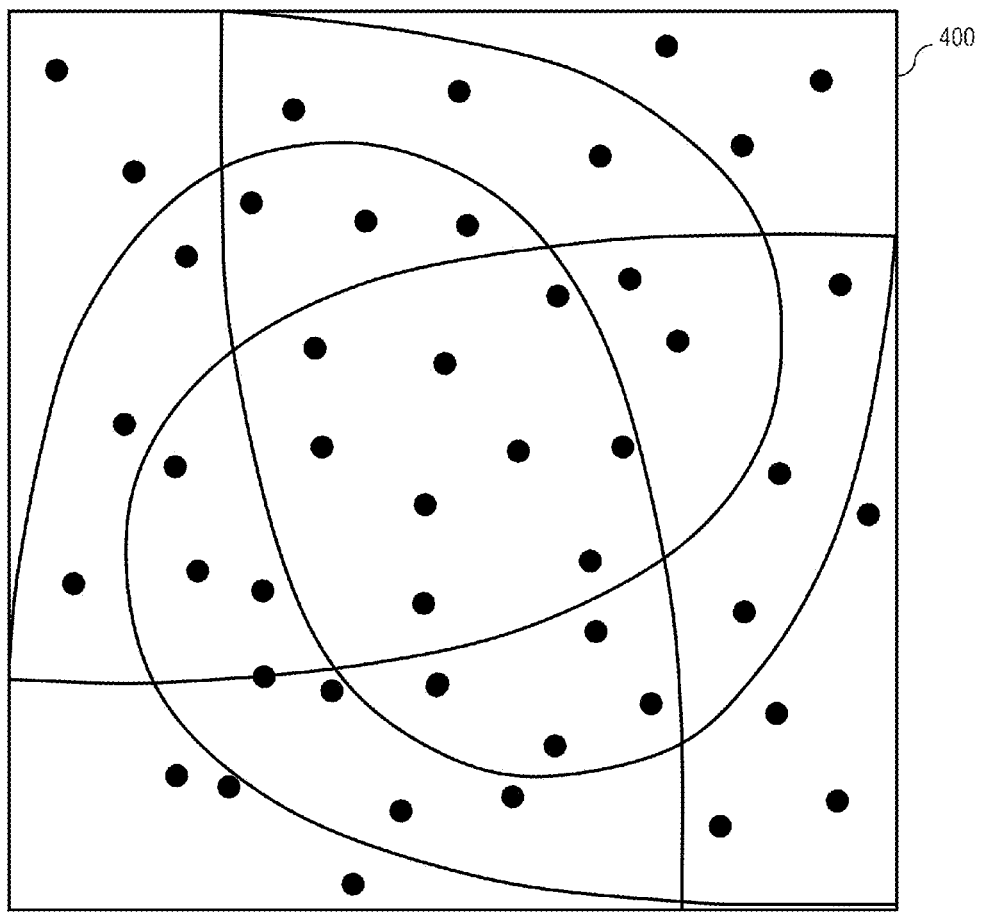
FIG. 4 is an exemplary illustration of adaptive sampling to capture information about a material's local state at locations sketched in black points within a feature of interest surrounded by black boundaries, according to aspects of the present disclosure.

Referring briefly to FIG. 4, for the morphology captured in FIG. 3, an illustration 400 demonstrates the use of adaptive sampling to select targeted points at which to capture information about a material's local state at locations sketched in black points, within a feature of interest surrounded by black boundaries.

Referring back to FIG. 2, the captured crystallographic orientation information is used in a rendering process at 212 to fill in the non-targeted spatial locations with the feature of interest on the surface of the material corresponding to the captured morphology to generate a rendered local state map at 214.

Figure 5:
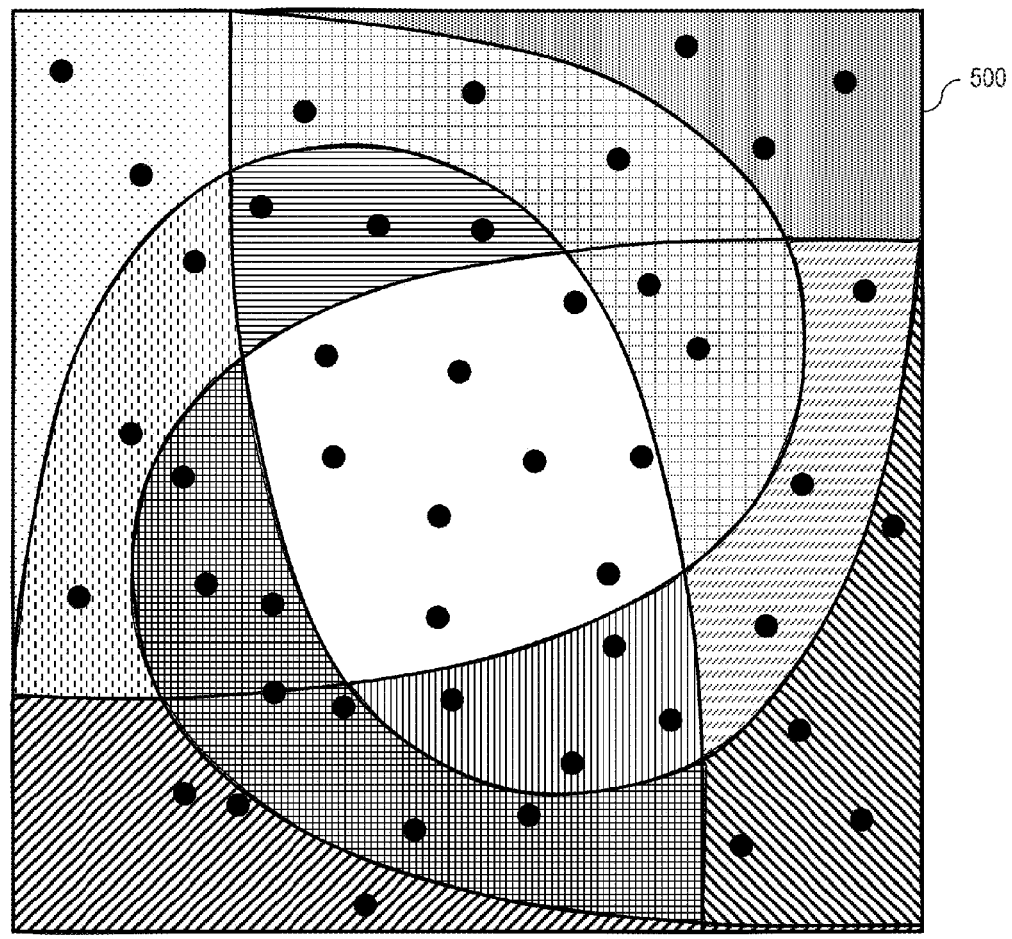
FIG. 5 is an exemplary illustration of building a rendered local state map by rendering areas within each feature of interest from FIG. 3 using selectively sampled local state information captured in FIG. 4, according to aspects of the present disclosure.

Referring briefly to FIG. 5, illustration 500 demonstrates building a rendered local state map by rendering areas within each feature of interest from FIG. 3 using the selectively sampled local state information captured in FIG. 4. For example, the state information at one point (e.g., pixel—including voxel, etc.) of a FoI can be used to fill in state information for all other points within the feature of interest.

Referring back to FIGS. 2-5 generally, for instance, data mining techniques, computer vision techniques, and/or image processing techniques can be utilized to evaluate the image or images captured from the morphology at 204. In this regard, the data mining may be utilized to identify grains or other spatially contiguous features of interest of the material. (As stated above, a grain is a type of feature of interest; as such, the examples herein directed toward grains may be applicable to other features of interests). More particularly, the boundaries of a FoI may be identified, e.g., using feature extraction or other suitable image processing techniques. As such, crystallographic orientation or other local state information can be captured at the selected targeted spatial locations within an identified FoI.

As an illustrative example, the adaptive sampling at 208 may include data mining of the captured morphology by optical microscopy to identify targeted regions defined by grains (or the boundaries of grains) on the surface of the material under evaluation. In this regard, local state data is collected at 210 in the form of crystallographic orientation information of the surface of the sample, which is captured at the selected targeted spatial locations by capturing the crystallographic orientation information of at least one pixel within the identified grains. That is, at least one pixel (but less than the total number of pixels within the grain in optical micrographs) is scanned to capture crystallographic orientation. Because the crystallographic orientation is likely to be similar within the boundaries of each grain (in the illustrative case of an annealed or un-deformed metallic material), and because the boundaries of the grain are known from the relatively inexpensive, but high resolution optical image, each pixel of the image within the boundaries of the grain can be filled in by the rendering process at 212, with the measured crystallographic orientation information that is taken within that grain.

For instance, crystallographic orientation can be captured at 210 using any prevailing technology, such as Rayleigh wave, scanning electron microscopy, Laue techniques, X-ray, ultrasound techniques, etc. As another example, data mining can be used analyze rendered local states.

Accordingly, various aspects of the present disclosure provide for adaptive data collection of the local states of a sample under evaluation by capturing a morphology (e.g., of various constituents on a surface or within the bulk) of a material under evaluation. Targeted regions are selected (i.e., features of interest) on the surface (or inside the bulk) of the material under evaluation based upon the captured morphology, and detailed information on the local state (e.g., crystallographic orientation) of the surface of the sample is collected at the selected targeted regions. The captured local state information is used to fill in the non-targeted regions of the surface of the material within the feature of interest corresponding to the captured morphology.

However, the approaches herein provide algorithms to increase the data collection speed and resolution during large area scans, e.g., EBSD scans. Notably, grains in 2-dimensional EBSD maps of single phase metallic alloys appear as a group of pixels with same crystallographic orientation bordered by grain boundaries. The morphology of a grain is identified by its grain boundaries and its orientation can be identified by a single point within the grain boundary because all other pixels inside the grain boundary have the same or similar orientation. Thus, methods herein derive grain boundaries and a small number of points per grain to record the microstructure (morphology and crystallography).

As such, the microstructure may be recorded by capturing a morphology of features of interest of a material under evaluation, capturing information giving the local state of the material under evaluation at various spatial locations within locations defining the features of interest, and using the obtained local state information to fill spatial locations of the material under evaluation where local state information is not obtained, and which corresponds to the captured morphology. In other words, the method fills in the areas corresponding to the features of interest for which the local state information was not previously captured.

In this regard, local state information may be obtained through location sampling by selecting targeted spatial locations based upon the captured morphology. In this example, adaptive recording of local state information may be carried out by capturing information giving the local state at the selected targeted spatial locations, such as a point or group of points within each feature of interest.

The method may also comprise performing a rendering operation using the captured local state information to fill in the non-targeted spatial locations of the material under evaluation. For instance, rendering may be performed by assigning the crystal orientation captured at targeted spatial locations to all other pixels within the same grain boundary using data fusion. By decoupling morphological data collection from orientation data collection, high resolution/fast methods may be utilized for morphological data collection such as optical microscopy or backscattered election imaging. For the expensive/slow/low-spatial resolution local state (e.g., orientation) recording, the method uses a small number of selected points per grain. For instance, in illustrative implementations less than 3% of the total area scanned may be evaluated for local state information.

An illustrative implementation of the methods herein demonstrates the increase in resolution and speed compared to alternative approaches. Assume an EBSD scan is to be performed to cover a 170 µm×200 µm area at 0.25 µm step size (544,000 pixel) with a data collection speed of 200 measurements per second (mps) using conventional techniques, giving a total time for data collection of about 0.76 hr. This scanned data will include salient details of the local state (e.g., crystallography) and morphology for the scanned area.

Referring generally to FIGS. 6-9, aspects of the present disclosure demonstrate the increase in resolution and speed compared to conventional approaches.

Figure 6:
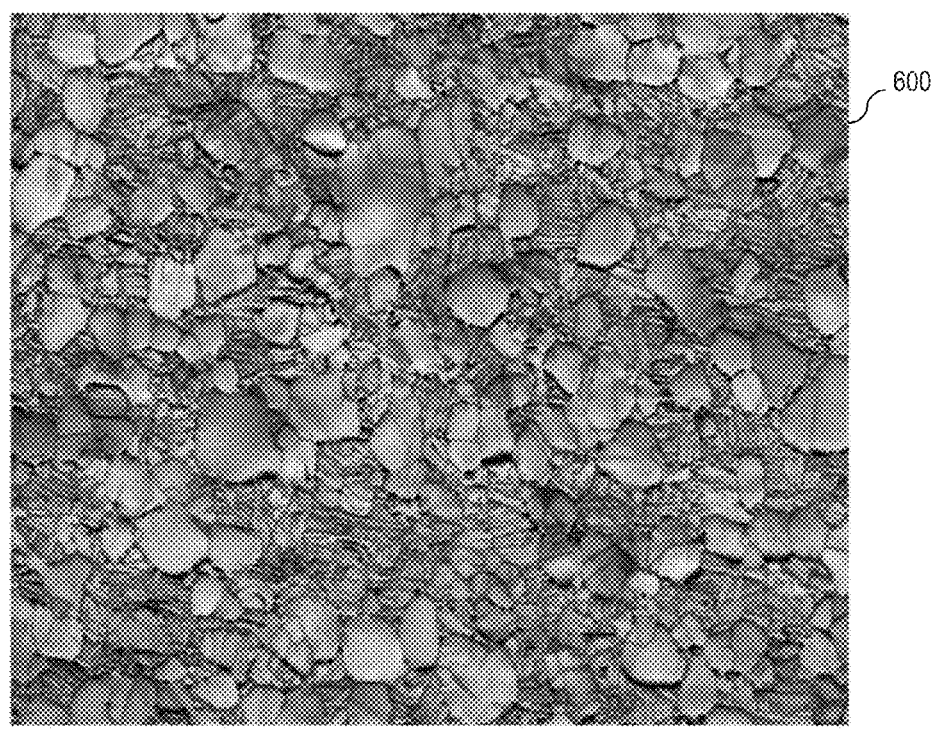
FIG. 6 is an exemplary micrograph for a titanium surface, according to aspects of the present disclosure.

Referring now to FIG. 6, an exemplary micrograph 600 is shown for a titanium surface with the given dimensions of the above example. This micrograph, with a size 680 pixels× 800 pixels, is collected, for instance, as a secondary electron image in 60 seconds.

Figure 7:
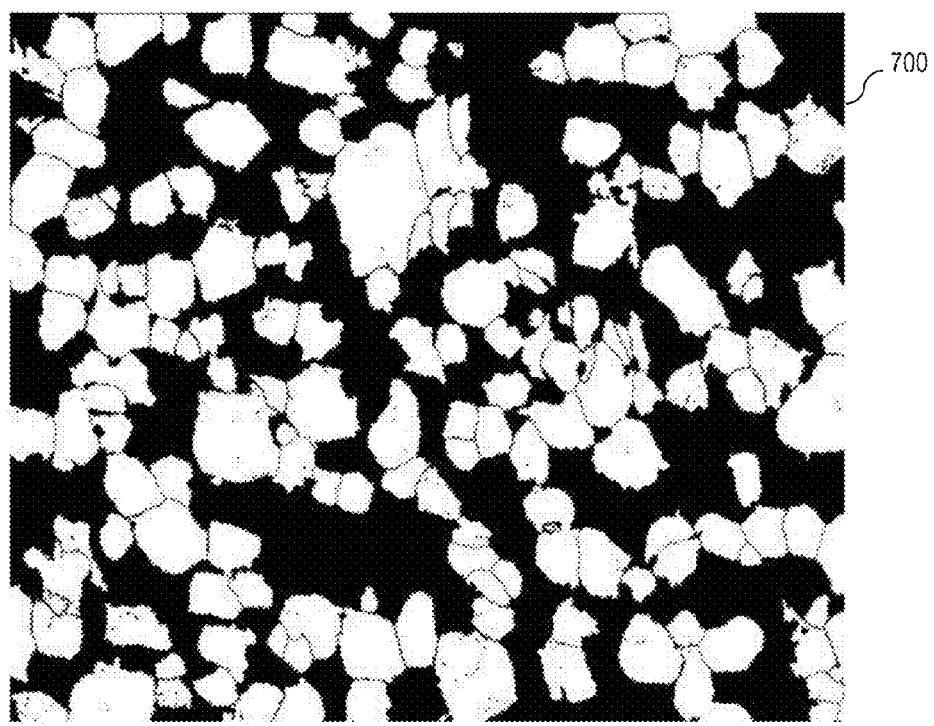
FIG. 7 is an example of identifying a morphology of features of interest within the micrograph of FIG. 6, according to aspects of the present disclosure.

Referring now to FIG. 7, assume the features of interest are primary alpha ($\alpha_p$) grains with an average size of 10 µm. Using the methods herein, the morphology of features of interest within the micrograph are identified as illustrated by 700, giving 189 $\alpha_p$ grains total over the scanned area.

Figure 8:
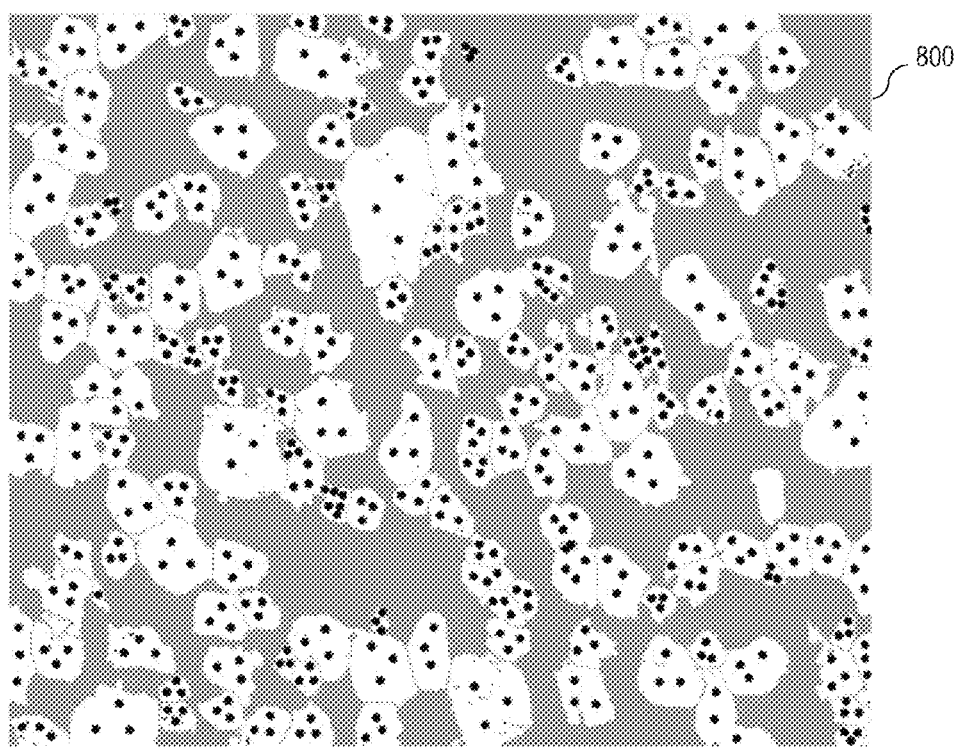
FIG. 8 is an example of identifying locations to collect local state data using the morphology of FIG. 7, according to aspects of the present disclosure herein.

Referring now to FIG. 8, by using the methods herein, local state (e.g., orientation) data is collected, for instance, at only 3 targeted points per grain (567 pixels) indicated by black circles within the grains as illustrated at 800. Assuming the same 200 mps, this will take less than 3 seconds for EBSD data collection.

Figure 9:
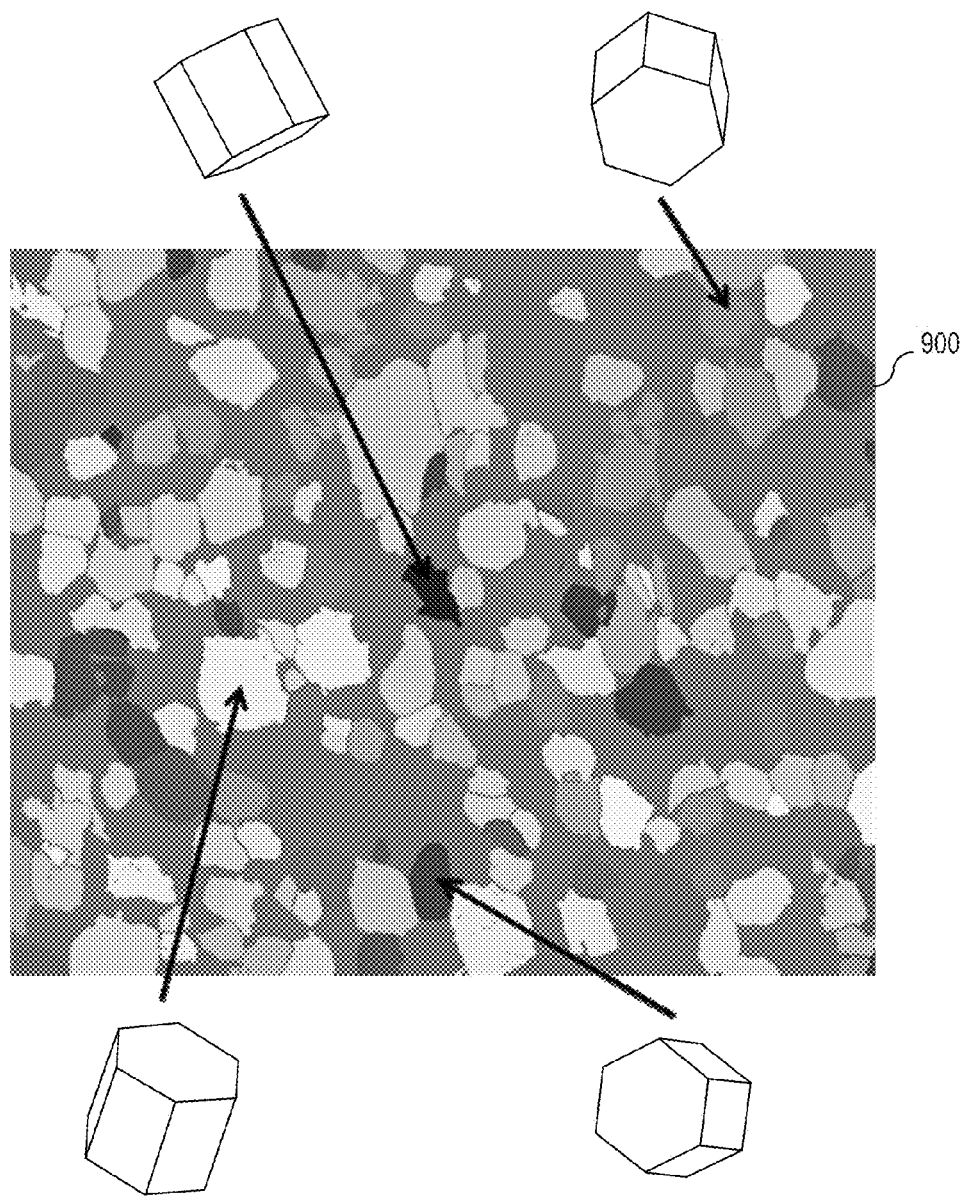
FIG. 9 is an example of a rendering operation of a dataset corresponding to the titanium surface processed with reference to FIGS. 6-8.

Referring now to FIG. 9, using the methods herein, a rendering operation is used to fill the grains in the SE image 900 by using captured EBSD data from the targeted locations. The orientation of the hexagonal crystal structure is shown schematically for selected grains. This operation will take less than 60 seconds, resulting in a combined dataset with the same 0.25 µm resolution in less than 130 seconds total time, giving an effective data collection rate of 4200 mps, a net 95% decrease in data collection time as compared to the conventional art.

Similarly, in another exemplary illustration, a 10 mm×10 mm ADC/EBSD dataset collected at a 1 µm effective resolution and comprising 1600 individual measurement tiles with dimensions 250 µm×250 µm would take less than 17 hours using the methods and processes set out herein, compared to more than 6 days at the same resolution using conventional art, giving an 89% reduction in scan time without any changes to hardware. Spatial location selection for adaptive sampling can be done in various ways, e.g., a regular grid, pattern recognition, employing 2-point correlations, etc.

Tasks such as quantifying microstructure heterogeneities and extracting outliers require covering large areas of a sample surface with a high resolution investigation. Such tasks also require collecting both local state (e.g., crystallographic orientations) and morphological information. However, the collection of such information is slow and expensive. The disclosure herein, provides methods and processes to significantly speed up such applications, as described more fully herein.

Figure 10:
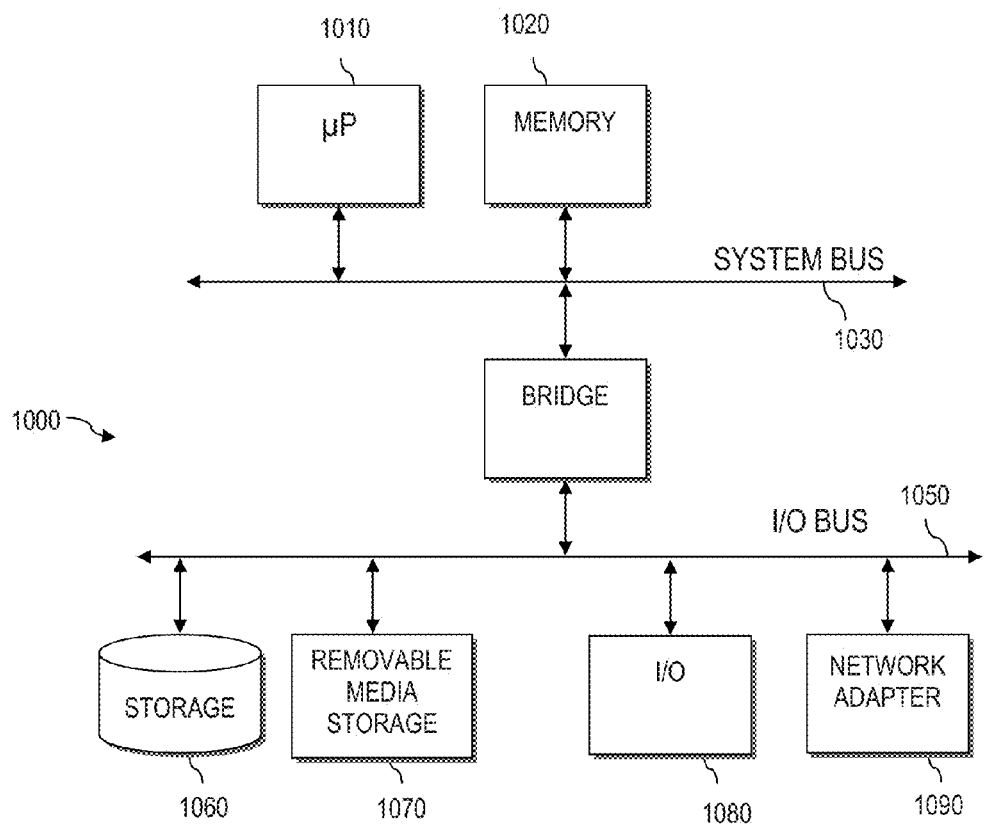
FIG. 10 is a diagram of an exemplary computer processing system for implementing the methods and processes described more fully herein.

Miscellaneous:

Referring to FIG. 10, a schematic of an exemplary computer system having computer readable program code for executing aspects described herein with regard to the preceding FIGURES. The computer system 1000 includes one or more microprocessors 1010 that are connected to memory 1020 via a system bus 1030. A bridge 1040 connects the system bus 1030 to an I/O Bus 1050 that links peripheral devices to the microprocessor(s) 1010. Peripherals may include storage 1060, such as a hard drive, removable media storage 1070, e.g., floppy, flash, CD and/or DVD drive, I/O device(s) 1080 such as a keyboard, mouse, etc. and a network adapter 1090.

The memory 1020, storage 1060, removable media insertable into the removable media storage 1070 or combinations thereof, can be used to implement the methods, configurations, interfaces and other aspects set out and described herein. Thus, the computer system 1000 may be used to implement a machine-executable method for capturing features of interests in materials, according to one or more of the methods set out herein. In this regard, the memory 1020, storage 1060, removable media insertable into the removable media storage 1070 or combinations thereof, can implement computer-readable hardware that stores machine-executable program code for capturing features of interests in materials, wherein the program instructs a processor (e.g., microprocessor 1010) to perform one or more of the methods set out herein.

Still further, the exemplary computer system may be implemented as an apparatus for capturing features of interests in materials, which may comprise a processor (e.g., microprocessor 1010) coupled to a memory (e.g., memory 1020, storage 1060, removable media insertable into the removable media storage 1070 or combinations thereof), wherein the processor is programmed for capturing features of interests in materials by executing program code to perform one or more of the methods set out herein.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device, e.g., the system described with reference to FIG. 10. A computer readable storage medium, as used herein, is not to be construed as being transitory signals per se, such as radio waves or other freely propagating electromagnetic waves through a transmission media.

Computer readable program instructions described herein can be downloaded to respective computing/processing devices from a computer readable storage medium or to an external computer or external storage device via a network, for example, the Internet, a local area network, a wide area network and/or a wireless network.

The flowchart and block diagrams in the Figures illustrate the architecture, functionality, and operation of possible implementations of systems, methods and computer program products according to various aspects of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Computer program code for carrying out operations for aspects of the present disclosure may be written in any combination of one or more programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Aspects of the present disclosure are described herein with reference to flowchart illustrations and/or block diagrams of methods, apparatuses (systems) and computer program products according to embodiments of the disclosure. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable instruction execution apparatus, create a mechanism for implementing the functions/acts specified in the flowchart and/or block diagram block or blocks.

These computer program instructions may also be stored in a computer readable medium that when executed can direct a computer, other programmable data processing apparatus, or other devices to function in a particular manner, such that the instructions when stored in the computer readable medium produce an article of manufacture including instructions which when executed, cause a computer to implement the function/act specified in the flowchart and/or block diagram block or blocks. The computer program instructions may also be loaded onto a computer, other programmable instruction execution apparatus, or other devices to cause a series of operational steps to be performed on the computer, other programmable apparatuses or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular aspects only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of any means or step plus function elements in the claims below are intended to include any disclosed structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The aspects of the disclosure herein were chosen and described in order to best explain the principles of the disclosure and the practical application, and to enable others of ordinary skill in the art to understand the disclosure with various modifications as are suited to the particular use contemplated.

What is claimed is:

1. A method of capturing local states within features of interests in materials, comprising:
   capturing a morphology of features of interest of a material under evaluation;
   obtaining information giving the local state of the material under evaluation at various spatial locations that correspond to the captured morphology; and
   using the obtained local state information to fill spatial locations of the material under evaluation where local state information was not obtained, at locations that correspond to the captured morphology.

2. The method of claim 1, wherein capturing a morphology comprises capturing a morphology on at least one of a surface of the material under evaluation, and within an interior of the material under evaluation.

3. The method of claim 1 further comprising:
   selecting targeted spatial locations of the material under evaluation based upon the captured morphology;
   wherein:
   obtaining information giving the local state of the material under evaluation comprises:
      capturing information giving the local state of the material under evaluation at the selected targeted spatial locations.

4. The method of claim 3, wherein selecting targeted spatial locations comprises selecting targeted spatial locations on at least one of a surface of the material under evaluation, and within an interior of the material under evaluation.

5. The method of claim 1, wherein capturing information giving the local state of the material under evaluation comprises capturing information giving the local state on at least one of a surface of the material under evaluation, and within an interior of the material under evaluation.

6. The method of claim 1, wherein capturing a morphology comprises capturing the morphology using at least one of light microscopy and electron microscopy.

7. The method of claim 1, wherein capturing a morphology comprises capturing the morphology of features of interest associated with a select one of a polished surface, unpolished surface, an etched surface, and an interior of the material.

8. The method of claim 1, wherein capturing a morphology comprises capturing the morphology associated with at least one of a mechanical model, electrical model, thermodynamic model, crystallographic model, thermal model, and acoustic model.

9. The method of claim 1, wherein selecting targeted spatial locations comprises selecting targeted spatial locations on at least one of the surface of the material under evaluation and the inside of the material under evaluation, based upon the captured morphology by data mining the captured morphology to identify targeted features of interest and targeted spatial locations.

10. The method of claim 1, wherein selecting targeted spatial locations comprises data mining the captured morphology to identify at least one of grains, particles and other regions containing similar or nearly similar local state, which can be either on the surface or in the interior of the material under evaluation.

11. The method of claim 1, wherein selecting targeted spatial locations comprises capturing crystallographic orientation information of the surface of the sample at the selected targeted regions by capturing the crystallographic orientation information for at least one pixel in each identified feature of interest.

12. The method of claim 1, wherein selecting targeted spatial locations comprises capturing chemistry information of the surface of the sample at the selected targeted regions by capturing the chemistry information for at least one pixel in each identified feature of interest.

13. The method of claim 1, wherein selecting targeted spatial locations comprises data mining the captured morphology to identify the boundaries of features of interest, which can be either on the surface or in the interior of the material under evaluation.

14. The method of claim 1, wherein capturing information giving the local state of the material under evaluation comprises capturing at least one of crystallographic orientation and chemistry information, of the surface of the sample at the selected targeted regions by capturing at least one of crystallographic orientation and chemistry information for at least one pixel identified within the boundary of an identified feature of interest.

15. The method of claim 1, wherein capturing information giving the local state of the material under evaluation comprises capturing crystallographic orientation of the surface of the sample by gathering crystallographic orientations by electron microscopy techniques.

16. The method of claim 1, wherein capturing information giving the local state of the material under evaluation comprises capturing crystallographic orientation information of the surface of the sample by gathering crystallographic orientations by Rayleigh wave technique.

17. The method of claim 1, wherein capturing information giving the local state of the material under evaluation comprises capturing crystallographic orientation information of the surface of the sample by gathering crystallographic orientations by Laue techniques.

18. The method of claim 1, wherein capturing information giving the local state of the material under evaluation comprises capturing crystallographic orientation information of the surface of the sample by gathering crystallographic orientations by x-ray diffraction techniques.

19. The method of claim 1, wherein capturing information giving the local state of the material under evaluation comprises capturing crystallographic orientation information of the surface of the sample by gathering crystallographic orientations by ultrasound techniques.

20. The method of claim 1, wherein capturing information giving the local state of the material under evaluation comprises capturing crystallographic orientation information of the surface of the sample by capturing crystallographic orientation information at a lower spatial resolution than that used to capture the morphology.

* * * * *